United States Patent [19]
Kupka et al.

[11] Patent Number: 6,030,370
[45] Date of Patent: Feb. 29, 2000

[54] SURGICAL INSTRUMENT

[75] Inventors: Thomas Kupka, Winnenden; Joachim Rein, Korntal; Johannes Solf, Sindelfingen; Manfred Dworschak, Duerbheim; Theodor Lutze, Balgheim, all of Germany

[73] Assignee: Aesculap AG and Co. KG, Tuttlingen, Germany

[21] Appl. No.: 09/014,219

[22] Filed: Jan. 27, 1998

[30] Foreign Application Priority Data

Feb. 5, 1997 [DE] Germany .......................... 197 04 261

[51] Int. Cl.⁷ .................................................. A61M 5/00
[52] U.S. Cl. ........................................... 604/264; 604/104
[58] Field of Search ..................... 604/104, 118, 604/122, 245–249, 256, 93, 264, 268, 523, 533; 606/1, 191

[56] References Cited

U.S. PATENT DOCUMENTS

| | | |
|---|---|---|
| 341,142 | 5/1886 | Hamilton ............................. 604/104 |
| 4,447,227 | 5/1984 | Kotsanis . |
| 5,017,193 | 5/1991 | Fields ...................................... 604/270 |
| 5,716,347 | 2/1998 | Gibbs et al. ............................ 604/247 |
| 5,788,680 | 8/1998 | Linder .................................... 604/280 |

FOREIGN PATENT DOCUMENTS

WO 95/17127 6/1995 WIPO .
WO 95/17128 6/1995 WIPO .

*Primary Examiner*—Wynn Wood Coggins
*Assistant Examiner*—Deborah Blyveis
*Attorney, Agent, or Firm*—Barry R. Lipsitz; Ralph F. Hoppin

[57] ABSTRACT

In the performance of vascular anastomosis, in order to improve and simplify the making of the connection between the vessels, a surgical instrument is proposed which is characterized by a tubular shaft closed at the front end thereof, with an outer diameter which enables introduction into one of the vessels, with suction openings in the wall of the shaft in the area of the front end thereof, and with a suction connection on the shaft at a distance from the front end thereof.

14 Claims, 2 Drawing Sheets

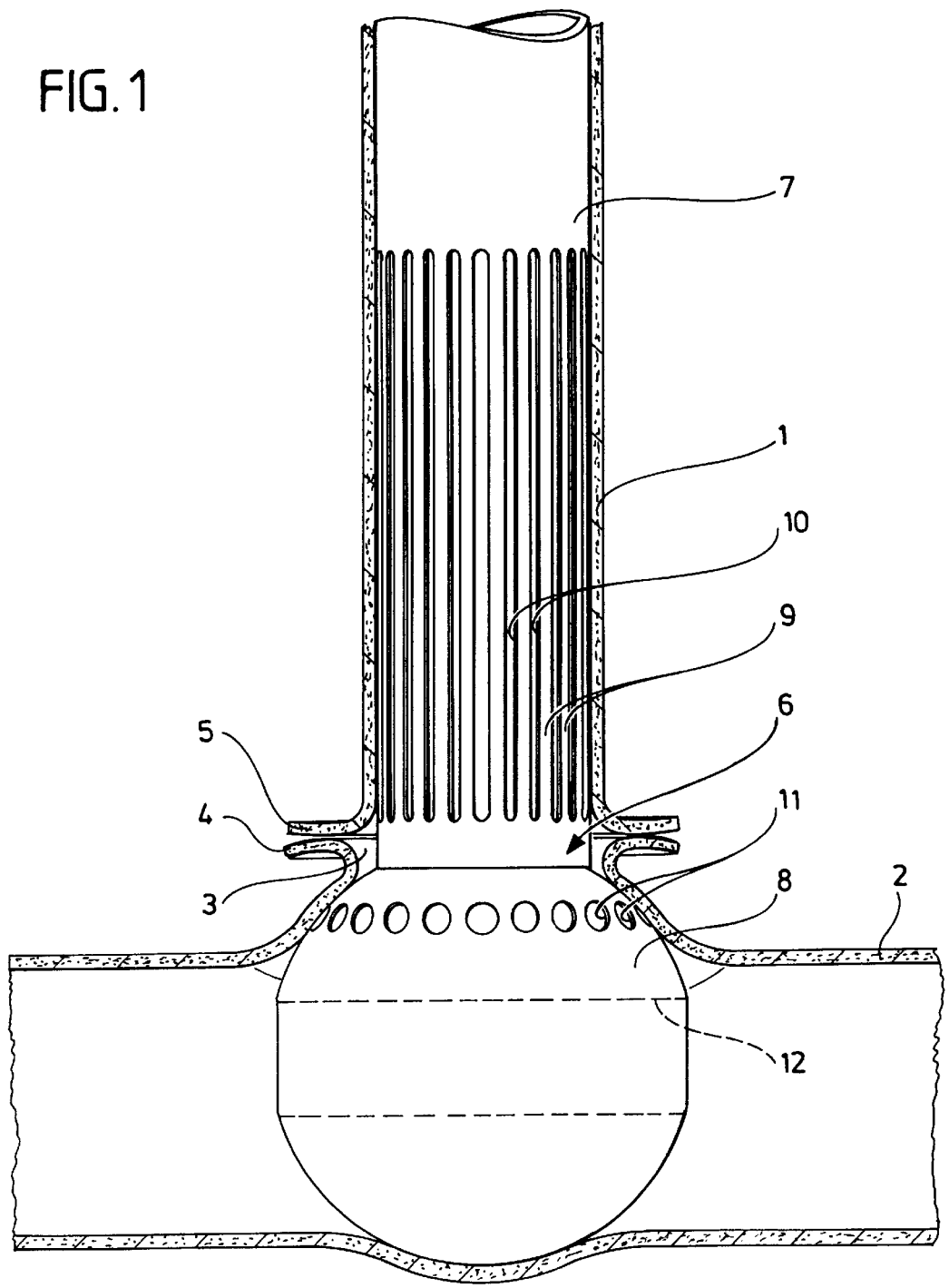

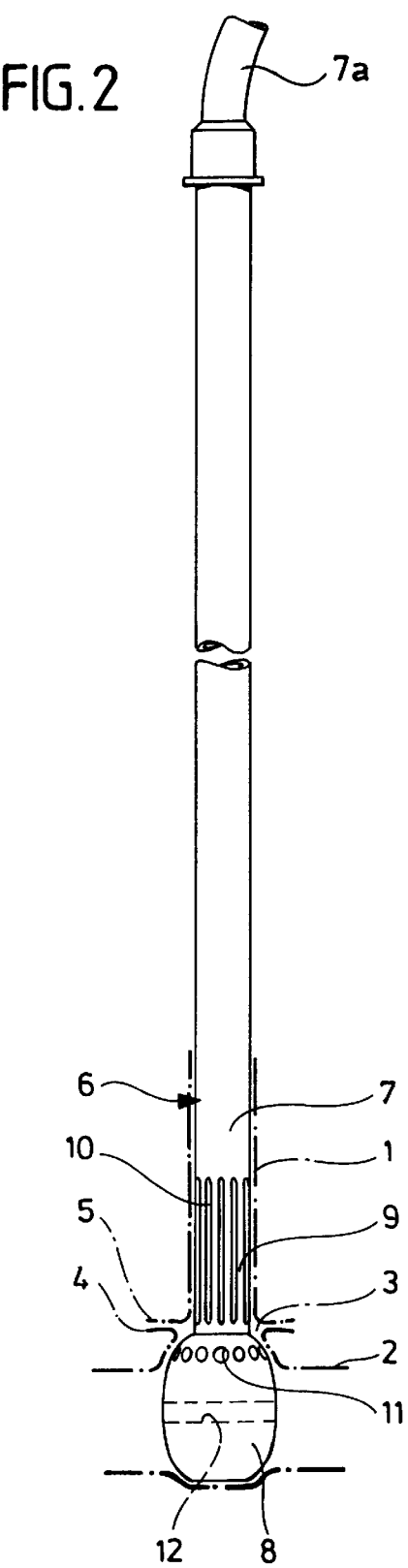
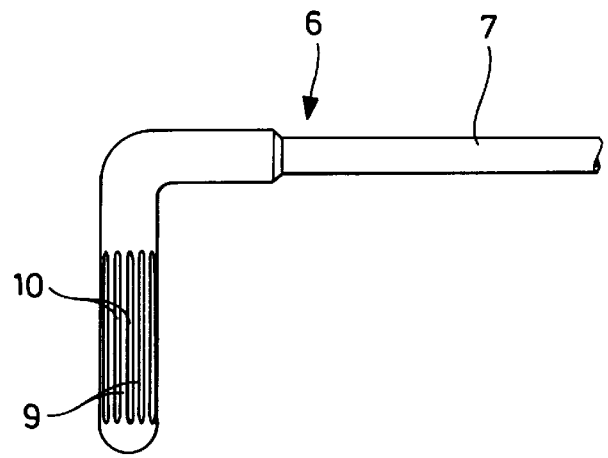
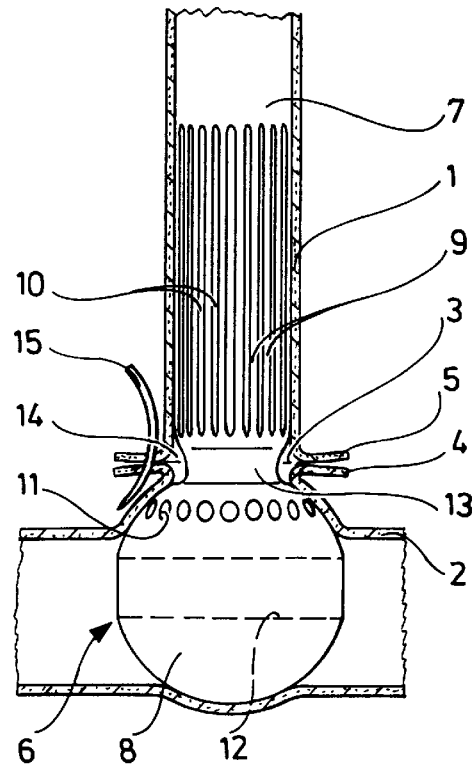

SURGICAL INSTRUMENT

The present disclosure relates to the subject matter disclosed in German application No. 197 04 261.9 of Feb. 5, 1997, the entire specification of which is incorporated herein by reference.

BACKGROUND OF THE INVENTION

The invention relates to a surgical instrument for performing vascular anastomosis.

In order to join vessels, their edges adhering to one another must be sewn together. This sewing technique makes high demands on the operating surgeon, especially in the microrange.

When joining a vessel piece to the side of a vessel, the vessel is usually perforated by stab incision. This incision can then be widened to the vessel diameter. The vessel piece to be joined is then positioned using forceps, and the first puncture is made with a needle. With the needle lying, the vessel piece to be joined is subsequently brought up to the incision in the other vessel, and, in this position, the first corner suture is made. It is mainly the cobbler's suture technique that is used here. The semicircles which are still open are then closed with a continuous suture.

This technique known per se demands high manual skill and a considerable amount of practice on the part of the operating surgeon. The long-term results of the operation depend mainly on the quality of the anastomosis. Imperfect transitions, contractions and the like often result in stenoses and swirls in the blood stream and hence in increased plaque formation.

SUMMARY OF THE INVENTION

The object of the invention is to provide a surgical instrument for simplifying the suturing with simultaneous improvement and reproducibility of the suturing quality.

This object is accomplished in accordance with the invention by a surgical instrument which is characterized by a tubular shaft closed at the front end thereof, with an outer diameter which enables introduction into one of the vessels, with suction openings in the wall of the shaft in the area of the front end thereof, and with a suction connection on the shaft at a distance from the front end thereof.

Such an instrument is pushed with its tubular shaft through the vessel piece to be attached so that the vessel piece surrounds the shaft and is held thereon. The shaft is introduced at its front end into the vessel which is to be connected to the vessel piece held on the shaft. The vessel to which the vessel piece is to be attached can be the end face of a vessel or an opening in the side wall of the vessel. Through the suction openings located in the wall of the shaft in the area of the front end thereof, both the wall of the vessel piece held on the shaft and the wall of the vessel into which the front end of the instrument is introduced are drawn in by suction against the wall of the shaft. The edges of the vessels which are to be sewn can now be brought with forceps into the desired position by the surgeon. In this position, the vessel edges are fixed relative to one another by the suction while the surgeon sews together the edges held firmly in this position. As the parts to be sewn together are fixed in their position, the quality of the suture is thereby significantly improved. It is further ensured that on piercing the vessel wall, the opposite vessel wall is not inadvertently caught. This is essential, particularly with vessels of small diameter, i.e., vessels with a diameter in the order of 1 or 2 millimeters.

Pressure lesions on the vein in the area of the intima are avoided by the drawing-in by suction. Also, the operating site remains easier to survey because there is no need for removal by suction to be carried out by third persons.

After completion of the suture, the suction is cut off and the instrument can be pulled in a simple way out of the vessel piece which is now attached. The attached vessel piece can then be sewn at the opposite end to another vessel. Again a suitable surgical instrument can be used here, but this is then introduced into the vessel piece through an opening in the side wall thereof.

It is expedient for the suction openings to be longitudinal slots which are distributed over the circumference. These longitudinal slots can additionally serve the surgeon as guide for the needle with which the suturing is carried out. Such guidance facilitates the suturing and also ensures that the number of punctures is evenly distributed over the circumference.

In accordance with a particularly preferred embodiment, provision is made for the shaft to have an enlargement at the front end thereof. This enlargement is introduced into the vessel to which the vessel piece held on the shaft is to be joined so the suture is made in the area of transition between the shaft and the enlargement. Such an enlargement is particularly advantageous when the vessel piece is to be joined to the side of a vessel as the enlargement then supports the side wall of the vessel from the inside.

The enlargement can, for example, be spherical or barrel-shaped.

In particular, provision is made for suction openings to be arranged in the wall of the enlargement. These then hold the wall of the vessel firmly in position. These suction openings can, for example, be in the form of a ring of circular openings which surround the entrance of the shaft into the enlargement.

It is also advantageous for the shaft to have suction openings, in particular, longitudinal slot-shaped suction openings, adjacent to the enlargement. These suction openings then serve to firmly position the vessel piece arranged on the shaft.

It is particularly advantageous for the shaft to taper in relation to its normal outer diameter in the area of transition in which it continues into the enlargement. In this area of transition in which the suture is made, this smaller outer diameter results in a free inner space in the area in which the suturing is to be carried out, and this free inner space makes it easier for the surgeon to puncture the vessel edges lying one on the other.

The enlargement can be of such configuration that it completely closes the vessel into which it is introduced. This helps to stabilize this vessel in the area of the suture.

In a preferred embodiment, provision is then made for the enlargement to have a flow-through channel which extends transversely to the longitudinal axis of the shaft and does not communicate with the shaft. This flow-through channel enables a flow through the vessel also during the sewing operation. The opening at the side is closed by the vessel edge resting firmly against the enlargement.

In particular, this flow-through channel can be closable, for example, by turning the enlargement through 90° or by a closure device, for example, a ball valve or any other closure valve known per se so that only intermittent flow through the site of the suture is possible.

While the shaft is usually of straight-line configuration, in a special embodiment provision may also be made for the shaft to be bent at an angle. This can make certain operating sites easier to reach with the shaft.

The instrument may consist of a resterilizable material, for example, of metal. It is, however, also possible for the instrument to be designed as a disposable component, and it is then preferably made of plastic.

The choice of diameter of the enlargement may vary in accordance with use. In particular, it is advantageous for a set of instruments with enlargements of different diameter to be provided, as instruments of various dimensions are then available to the operating surgeon, if required.

A more detailed explanation of the invention will be given in the following description of preferred embodiments taken in conjunction with the accompanying drawings:

BRIEF DESCRIPTION OF THE DRAWINGS

FIG. 1 a view in longitudinal section through two vessels to be anastomosed with an inserted surgical instrument fixing the two vessels firmly in position and having a spherical enlargement;

FIG. 2 a general view of the instrument of FIG. 1 with a barrel-shaped enlargement;

FIG. 3 an enlarged view of the front end area of the surgical instrument of FIG. 1 in an embodiment of reduced diameter in the area of transition continuing into the enlargement; and FIG. 4 a modified embodiment of a surgical instrument for performing vascular anastomosis with a shaft bent at an angle and without an enlargement.

DETAILED DESCRIPTION OF THE INVENTION

The invention will be explained hereinbelow with reference to an end-to-side vascular anastomosis by way of example, i.e., the joining of a vessel piece 1 of finite length to a continuous vessel 2, with the end of the vessel piece 1 being attached to the side of the vessel 2.

To this end, an opening 3 is made in the side wall of the vessel 2, for example, by an incision which is then widened, for example, in the form of a circle with a punching tool. The diameter of the opening is adapted to the inner diameter of the vessel piece 1.

In order to join the vessel piece 1 and the vessel 2, these are sewn together along the edge 4 of the opening 3 and along the edge 5 of the vessel piece 1. This sewing can be done conventionally with needle and thread or with a clip apparatus which in order to join the two edges 4 and 5 applies clips along these edges. The joining is preferably carried out by turning over the edges 4, 5 outwards so that the wall areas adjoining the edges lie surface-to-surface on one another, as shown in FIG. 1. This procedure is practically only possible using this technique.

A surgical instrument 6 which essentially comprises a tubular shaft 7 opening at its free end into a spherical enlargement 8 (FIG. 1) is used for making this connection of the edges 4 and 5. The shaft 7 communicates in the manner shown in FIG. 2 with a suction device 7a so a vacuum can be generated in its hollow inner space. The wall area 9 of the shaft 7 immediately adjoining the enlargement 8 is perforated by longitudinal slots 10 which extend parallel to the longitudinal axis of the shaft 7 and are distributed over the circumference thereof. In the embodiment of FIG. 1, the longitudinal slots 10 extend almost as far as the spherical enlargement 8. In the upper area of the spherical enlargement 8 immediately adjoining the shaft 7 there are arranged in the outer wall thereof circular openings 11 which connect the inner space of the spherical enlargement 8 with the outer space and surround the entrance of the shaft 7 into the spherical enlargement in the shape of a ring. The inner space of the enlargement 8 communicates with the shaft 7 so both the longitudinal slots 10 and the openings 11 act as suction openings to generate a vacuum in the shaft 7.

In the embodiment shown in FIG. 1, the spherical enlargement 8 has a flow-through channel 12 which extends through the center of it and is closed off from the inner space of the spherical enlargement 8. This flow-through channel 12 can serve to enable a flow through the spherical enlargement 8. This flow-through channel 12 is shown in the embodiment of FIG. 1, but it is readily possible to construct the spherical enlargement 8 without such a flow-through channel 12, i.e., to close it on all sides except for the openings 11.

The outer diameter of the shaft 7 is selected such that the vessel piece 1 can be pulled onto the shaft 7. As the vessel pieces to be used have different diameters, it is purposeful to provide a set of shafts 7 with a different outer diameter, for example, with outer diameters of 1 mm to 3 mm.

Similarly, the diameter of the spherical enlargement 8 can be chosen so as to accommodate the dimensions of the vessel 2. In principle, it is even possible to connect enlargements 8 with a different outer diameter to shafts 7 with various outer diameters, for example, by screwing them together.

The instrument 6 described above is used in the following way to make a suture between vessel piece 1 and vessel 2:

The vessel piece 1 is first pulled onto the shaft 7, more precisely, such that the edge 5 of the vessel piece 1 lies in the area of transition from the shaft 7 to the enlargement 8. The spherical enlargement 8 is then pushed through the side opening 3 into the vessel 2. The edges 4 and 5 of the vessel 2 and the vessel piece 1, respectively, are subsequently brought into a position relative to each other in which they can be sewn well, i.e., in which they are, for example, turned over outwards and placed surface-to surface against each other, as shown in FIG. 1. Once this position has been assumed, the shaft 7 is connected to the suction source so that both the vessel piece 1 and the vessel 2 are drawn in by suction via the longitudinal slots 10 and the openings 11 onto the shaft 7 and the enlargement 8, respectively, and thereby fixed. In this fixed position, the edges 4 and 5 can then be joined together by means of conventional sewing techniques or by means of clips, and the relative position of the edges 4 and 5 is substantially maintained during the sewing operation by the fixing.

During the sewing operation, the flow in the vessel 2 can be at least partially maintained if a flow-through channel 12 is provided in the enlargement 8. This flow can be cut off by turning the enlargement 8 through 90°, and, optionally, also by closure valves, not shown in the drawings, in the flow-through channel 12.

When joining the edges 4 and 5 with needle and thread, the longitudinal slots 10 can in addition to the suction function also assume a guiding function for the needle. Bent needles which are inserted into a longitudinal slot 10 and are guided thereon are normally used. This facilitates the precise piercing of the edges 4 and 5 and also ensures uniform distribution of piercing points along the circumference of the edges 4 and 5.

Once the sewing has been completed, the shaft 7 is separated from the suction source again and pulled out of the vessel piece 1, during which the walls of the vessel 2 and the vessel piece 1 are elastically expanded.

The geometry of the instrument 6 can be altered within certain limits. In the embodiment of FIG. 2, for example, which corresponds substantially to that of FIG. 1, and in which like parts have like reference numerals, the enlargement 8 is not of spherical configuration, but elongate. It is roughly barrel-shaped.

In the embodiment of FIG. 3, which again corresponds substantially to that of FIG. 1, the shaft 7 is of constricted design in the area between the longitudinal slots 10 and the entrance into the spherical enlargement 8. This constricted area 13, in which there are no suction openings, forms between the wall of the vessel 2 and the vessel piece 1 a free annular space 14 which facilitates the piercing of the edges 4 and 5 with a needle 15.

In the embodiment of FIG. 4, the shaft 7 is bent at an angle so that it is possible, in spite of places which are difficult of access, to still insert such an instrument. Also, in this simplified embodiment only a shaft 7 closed off at its front end, but not an enlargement 8, is provided with longitudinal slots 10. In this case, too, the instrument of simplified design can be inserted similarly to the instrument 6 described above. In this case, the free end of the shaft 7 enters the vessel 2, and the longitudinal slots 10 fix both the vessel 2 and the vessel piece 1. This technique is employable in both heart surgery and general vascular surgery.

The modifications described above can also be applied singly or in combination to the other embodiments.

What is claimed is:

1. A surgical instrument for performing vascular anastomosis, comprising:
   a tubular shaft closed at a front end thereof, with an outer diameter which enables the shaft to be introduced into a first vessel,
   suction openings in a wall of said shaft in an area of the front end thereof, and
   a suction connection on said shaft at a distance from the front end thereof, wherein:
      said suction openings communicate with the suction connection to provide a suction for drawing in a wall of the first vessel against the wall of the shaft to fix a position of the first vessel with respect to said shaft;
      said suction openings comprise longitudinal slots distributed over a circumference of said shaft;
      said shaft has an enlargement at the front end thereof;
      additional suction openings are arranged in a wall of said enlargement; and
      the shaft's suction openings are arranged in said shaft adjacent to said enlargement.
2. An instrument as defined in claim 1, wherein:
   said enlargement is spherical.
3. An instrument as defined in claim 1, wherein:
   said enlargement is barrel-shaped.
4. An instrument as defined in claim 1, wherein:
   said shaft tapers in relation to its normal outer diameter in an area of transition continuing into said enlargement.
5. An instrument as defined in claim 1, wherein:
   said shaft is bent at an angle.
6. An instrument as defined in claim 1, wherein:
   said enlargement has a flow-through channel which extends transversely to a longitudinal axis of said shaft and does not communicate with said shaft.
7. An instrument as defined in claim 6, wherein:
   said flow-through channel is closable.
8. An instrument as defined in claim 1, wherein:
   the instrument comprises resterilizable material.
9. An instrument as defined in claim 1, wherein:
   the instrument is designed as a disposable component.
10. A set of instruments as defined in claim 1, wherein:
    the instruments of one set have enlargements of different diameters.
11. An instrument as defined in claim 1, wherein:
    said longitudinal slots are evenly distributed over said circumference to provide a guide to a surgeon for providing punctures in the first vessel for suturing the first vessel to a second vessel.
12. An instrument as defined in claim 1, wherein:
    such enlargement is adapted to be inserted into a side opening of a second vessel to fix a position of the second vessel with respect to the first vessel.
13. An instrument as defined in claim 12, wherein:
    the shaft is positionable in the first vessel, and the enlargement is positionable in the second vessel such that edges of the first and second vessels are turned over outwards from the shaft and brought into a surface-to-surface position to be joined together.
14. A surgical instrument for performing vascular anastomosis, comprising:
    a tubular shaft closed at a front end thereof, with an outer diameter which enables the shaft to be introduced into a first vessel,
    suction openings in a wall of said shaft in an area of the front end thereof, and
    a suction connection on said shaft at a distance from the front end thereof, wherein:
       said suction openings communicate with the suction connection to provide a suction for drawing in a wall of the first vessel against the wall of the shaft to fix a position of the first vessel with respect to said shaft;
       said shaft has an enlargement at the front end thereof; and
       said enlargement has a closable flow-through channel which extends transversely to a longitudinal axis of said shaft and does not communicate with said shaft.

* * * * *